US00PP22365P2

(12) United States Plant Patent
Kapusta

(10) Patent No.: US PP22,365 P2
(45) Date of Patent: Dec. 20, 2011

(54) ***CLEMATIS* PLANT NAMED 'CLEMINOV 29'**

(50) Latin Name: *Clematis hybrida*
Varietal Denomination: Cleminov 29

(75) Inventor: Veronique Kapusta, Beaucouzé Cedex (FR)

(73) Assignee: Agri Obtentions S.A., Guyancourt Cedex (FR)

( * ) Notice: Subject to any disclaimer, the term of this patent is extended or adjusted under 35 U.S.C. 154(b) by 1 day.

(21) Appl. No.: 12/805,475

(22) Filed: Aug. 2, 2010

(51) Int. Cl.
*A01H 5/00* (2006.01)

(52) U.S. Cl. ..... Plt./228
(58) Field of Classification Search ..... Plt./228
See application file for complete search history.

*Primary Examiner* — June Hwu
(74) *Attorney, Agent, or Firm* — Buchanan Ingersoll & Rooney PC

(57) ABSTRACT

A new and distinct variety of *Clematis* plant is provided that is the product of a controlled breeding program. Attractive light lavender flowers with flashes of magenta along the central portion of each tepal are formed on a substantially continuous basis over an extended period of time. The growth habit is compact and bushy and the plant well resists wilting and withering. The plant can be readily propagated by the use of cuttings and can be grown to advantage to provide colorful ornamentation in the landscape and in pots.

1 Drawing Sheet

Botanical/commercial classification: *Clematis hybrida*/ *Clematis* Plant.

Varietal denomination: cv. Cleminov 29.

SUMMARY OF THE INVENTION

A new and distinct *Clematis* plant is provided that is the product of a controlled interspecific hybridization program carried out at Angers, France. The female parent (i.e., the seed parent) was the *Clematis integrifolia* 'Olgae' variety (non-patented in the United States), and the male parent (i.e., pollen parent) was the 'The President' variety (non-patented in the United States). A single plant of the new variety of the present invention was selected primarily on the basis of the attractiveness of the flowers and the extremely long flowering season.

It was found that the new *Clematis* variety of the present invention displays the following combination of characteristics:

(a) exhibits a compact and bushy growth habit, (b) forms in abundance on a substantially continuous basis over an extended period of time attractive light lavender flowers with flashes of magenta along the central portion of each tepal, and (c) readily can be propagated by the use of cuttings.

The new variety commonly flowers on a substantially continuous basis for approximately 4 to 5 months on average from June to September which significantly exceeds the flowering period of many other *Clematis* varieties. Also, the new variety has been found to well resist the wilting and withering phenomenon commonly observed with respect to many previously known climbing *Clematis* varieties.

The new variety of the present invention well meets the needs of the horticultural industry and is particularly well suited for providing colorful ornamentation in the landscape and when grown in pots.

The new variety of the present invention can be readily distinguished from all other *Clematis* varieties of which I am aware including its parental varieties on the basis of the above-identified combination of characteristics. More specifically, the 'Olgae' variety forms smaller flowers which are displayed for a considerably shorter period of time. Also, 'The President' variety is considerably less compact in its growth habit and the duration of the blooming is considerably shorter.

The new variety is similar to the 'Cleminov 51' variety (United States Plant Pat. No. 17,012) in habit and form. Such 'Cleminov 51' variety was derived from a cross of the same parents. However, the flowers of the new variety are different in coloration. More specifically, the flowers of 'Cleminov 51' are very dark blue to purple in coloration, and the flowers of the new variety are two-toned and display light lavender coloration combined with flashes of magenta along the central portion of each tepal.

The new variety of the present invention has been found at Angers, France, to readily undergo asexual propagation by the rooting of cuttings. The distinctive combination of characteristics of the new variety is reliably transmitted to subsequent generations following such propagation. Accordingly, the new variety propagates true-to-type via asexual reproduction.

The new variety has been named 'Cleminov 29', and will be marketed under the DOUBLE ROSE Trademark.

BRIEF DESCRIPTION OF THE PHOTOGRAPH

The accompanying photograph shows typical blossoms and foliage of a one-year-old plant of the new variety during the summer while growing at Angers, France. The plant had been asexually reproduced by the rooting of cuttings. The attractive light lavender flowers with flashes of magenta along the central portion of each petal are illustrated.

DETAILED DESCRIPTION

The following description is based on the observation of one-year-old plants of the new variety while growing in a greenhouse near West Grove, Pa., U.S.A. during July, 2010.

The plants had been asexually reproduced by the rooting of cuttings. Color designations are with reference to The R.H.S. Colour Chart of the Royal Horticultural Society London, England. When employed common color terms are to be accorded their customary dictionary significance.

Origin: A product of the controlled cross of the 'Olgae' variety (female) and the 'The President' variety (male).

Plant:

*Habit.*—Compact and bushy.

*Height.*—Commonly approximately 85 cm on average when grown in a pot and approximately 100 cm on average when grown in the landscape.

*Width.*—Commonly approximately 20 cm on average when grown in a pot.

Branches:

*Color.*—Young stems: commonly near Greyed-Orange Group 176B. adult stems: commonly near Greyed-Orange Group 177A.

*Stem length.*—Commonly approximately 80 to 90 cm on average.

*Internode length.*—Varies somewhat with age of plant, and typically is approximately 9 cm on average.

Foliage:

*Leaf general appearance.*—Dense with a dull aspect (non-glossy).

*Leaf length.*—Commonly approximately 5 cm on average.

*Leaf width.*—Commonly approximately 2.5 cm on average.

*Leaf shape.*—Ovate to lanceolate.

*Leaf base.*—Obtuse to attenuate.

*Leaf apex.*—Generally cuspidate to acute.

*Leaf color.*—New foliage: upper surface: near Yellow-Green Group 144A. under surface: near Yellow-Green Group 144B. mature foliage: upper surface: near Green Group 137A. under surface: near Yellow-Green Group 147B.

*Petioles.*—Commonly approximately 1 cm in length, firm, and commonly near Yellow-Green Group 144B in coloration with the coloration sometimes varying with the location of the petiole along the stem.

Inflorescence:

*Number.*—Commonly approximately 9 on average per stem.

*Time of blooming.*—Commonly from June to September.

*Duration of blooming.*—Commonly approximately 4 months on average on a substantially continuous basis.

*Peduncle.*—Commonly approximately 2 cm in length on average, approximately 3 mm in diameter on average, and near Yellow-Green Group 145B in coloration.

*Buds.*—Urn-shaped, medium in size, commonly approximately 2.5 to 3 cm in length on average, approximately 1 cm in diameter on average, and near Red-Purple Group 70A in coloration.

*Size.*—A fully open individual flower commonly measures approximately 8 cm in diameter on average. The flower when fully open is relatively flat and of an insignificant depth.

*Configuration.*—Disc-shaped.

*Tepal number.*—Between 4 and 6 per flower and most commonly 6.

*Tepal length.*—Commonly approximately 4 cm on average.

*Tepal width.*—Commonly approximately 2 cm at the widest point on average.

*Tepal arrangement.*—Radial.

*Overall tepal shape.*—Elongated.

*Tepal apex.*—Pointed.

*Tepal margin.*—Entire.

*Tepal texture.*—Firm with superior resistance to wilting and withering.

*Tepal color.*—When fully open on the upper surface near Violet Group 84C with darker markings of Purple Group 78B towards the center of each petal, the under surface near Purple Group 76A with base and center near Purple Group 77A.

*Lastingness.*—A typical flower commonly lasts approximately 7 days on the plant on average.

*Fragrance.*—Very slight.

*Stamens.*—Approximately 56 on average.

*Pollen.*—Present and near Greyed-Purple Group 187B in coloration.

*Anthers.*—Near Greyed-Purple Group 187C in coloration, approximately 0.4 cm in length on average, and generally present in a ring arrangement.

*Filaments.*—Approximately 0.9 cm in length on average and commonly variable in coloration.

*Pistils.*—Approximately 10 in number on average.

*Styles.*—Near Green Group 142B in coloration and approximately 1.5 cm in length.

*Stigmas.*—Near Greyed-Purple Group 187C in coloration, and approximately 2 mm in length on average.

*Hips.*—Commonly feathery in configuration, tomentose, approximately 1.5 cm in length on average, approximately 1 cm in width on average, and near Yellow-Green Group 145C in coloration when mature.

*Seeds.*—Commonly one per hip, feathery in appearance, and near Greyed-Orange Group 175C in coloration when mature.

The disease resistance of the new cultivar during observations to date has been found to be comparable to that of *Clematis* plants in general with no particular disease or pest problems having been encountered during observations to date.

Plants of the new 'Cleminov 29' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Clematis* plant that exhibits the following combination of characteristics:

(a) exhibits a compact and bushy growth habit, (b) forms in abundance on a substantially continuous basis over an extended period of time attractive light lavender flowers with flashes of magenta along the central portion of each tepal, and (c) readily can be propagated by the use of cuttings; substantially as illustrated and described.

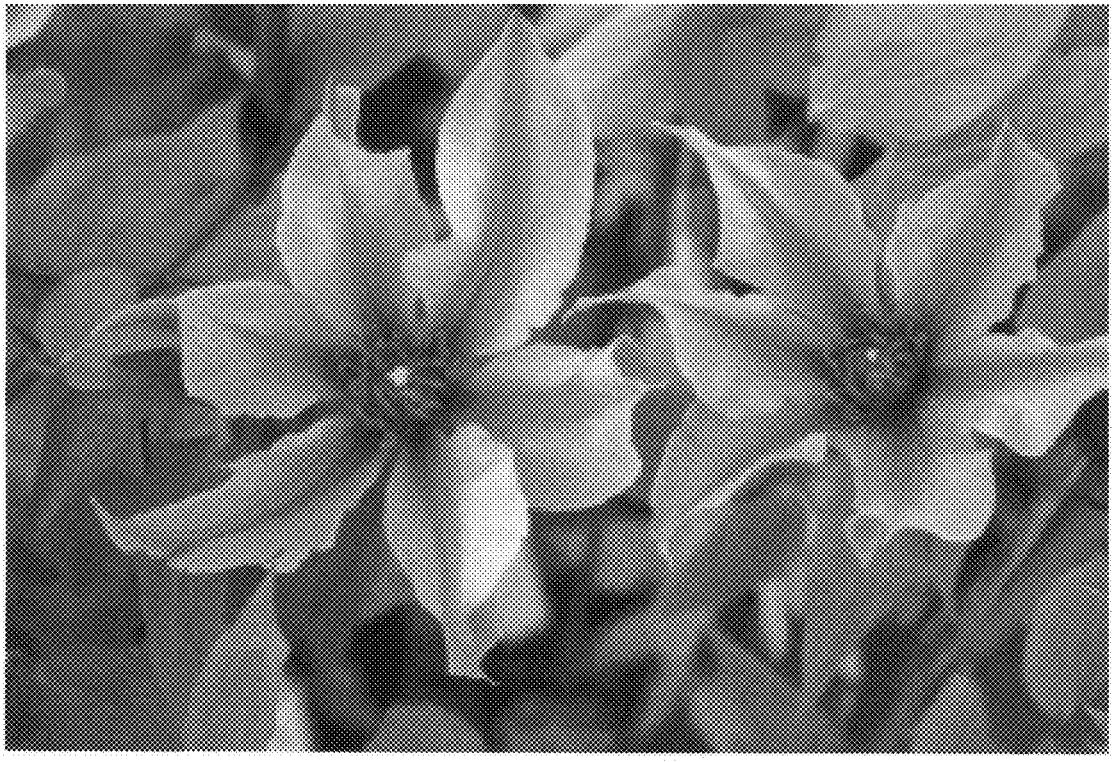

* * * * *